US005225408A

United States Patent [19]
Weller, III

[11] Patent Number: 5,225,408
[45] Date of Patent: Jul. 6, 1993

[54] BIPHENYL OXADIAZINONE ANGIOTENSIN II INHIBITORS

[75] Inventor: Harold N. Weller, III, Pennington, N.J.

[73] Assignee: E. R. Squibb & Sons, Inc., Princeton, N.J.

[21] Appl. No.: 811,373

[22] Filed: Dec. 20, 1991

[51] Int. Cl.$^5$ .................. A61K 31/535; C07D 273/04
[52] U.S. Cl. ..................................... 514/229.2; 544/68
[58] Field of Search ....................... 514/229.2; 544/68

[56] References Cited

U.S. PATENT DOCUMENTS

| | | | |
|---|---|---|---|
| 4,508,718 | 4/1985 | Sircar et al. | 514/238 |
| 4,812,462 | 3/1989 | Blankley et al. | 514/303 |
| 4,820,843 | 4/1989 | Aldrich et al. | 548/252 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |
| 5,064,825 | 11/1991 | Chakravarty et al. | 514/221 |

FOREIGN PATENT DOCUMENTS

| | | |
|---|---|---|
| 2027839 | 4/1991 | Canada . |
| 2033121 | 6/1991 | Canada . |
| 0324377 | 7/1989 | European Pat. Off. . |
| 0434249 | 6/1991 | European Pat. Off. . |

OTHER PUBLICATIONS

Chiu et al., European Journal of Pharmacology, 157 (1988) pp. 13–21.

*Primary Examiner*—Mukund J. Shah
*Assistant Examiner*—Matthew V. Grumbling
*Attorney, Agent, or Firm*—Timothy J. Gaul

[57] ABSTRACT

Angiotension II inhibition is exhibited by wherein:
$R^1$ and $R^2$ are each independently hydrogen, alkyl, aryl, aralkyl, cycloalkyl, cycloalkylalkyl, thiophenalkyl, pyridylalkyl, or —$R^8CO_2R^9$;
$R^3$ is a single bond, —S—, or —O—;
$R^4$ is hydrogen, alkyl, alkenyl, alkynyl, aryl, cycloalkyl, aralkyl, cycloalkylalkyl, or thiophenalkyl;
$R^7$ —$(CH_2)_n$—$CO_2R^9$, $$-CO_2CH(R^{12})-OC(O)-R^{13},$$

—$NHSO_2CF_3$, $$-O-S(O)(OH)-OH,$$

—$SO_3H$, —$C(CF_3)_2OH$, $$-O-P(O)(OH)-OH,$$

—$PO_3H$, $$NHP(O)(OH)-OH,$$

—$CONHOR^{12}$, —$CONHNHSO_2CF_3$, —$(CH_2)_n$—5—tetrazolyl (optionally substituted with $R^9$), $$-C(OH)(R^{15})-P(O)(OH)-OH,$$

a triazole with $CF_3$ substituent, or a triazole with $NR^9$, $R^{16}$ substituents;

and the remaining symbols are as defined in the specification.

13 Claims, No Drawings

BIPHENYL OXADIAZINONE ANGIOTENSIN II INHIBITORS

FIELD OF THE INVENTION

This invention relates to novel oxadiazinones that inhibit the action of angiotensin II, thus making them useful as antihypertensive agents.

BRIEF DESCRIPTION OF THE INVENTION

In accordance with the present invention, a compound of the formula

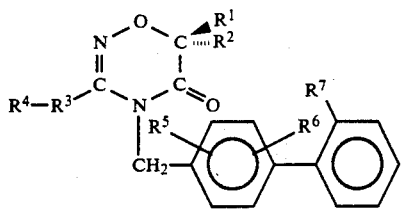

I and pharmaceutically acceptable salts and prodrugs thereof inhibit the action of angiotensin II. In compound I and throughout this specification, the symbols are defined as follows:

$R^1$ and $R^2$ are each independently hydrogen, alkyl, aryl, aralkyl, cycloalkyl, cycloalkylalkyl, thiophenalkyl, pyridylalkyl, or $-R^8CO_2R^9$;

$R^3$ is a single bond, $-S-$, or $-O-$;

$R^4$ is hydrogen, alkyl, alkenyl, alkynyl, aryl, cycloalkyl, aralkyl, cycloalkylalkyl, or thiophenalkyl;

$R^5$ and $R^6$ are each independently hydrogen, alkyl, alkoxy, halogen, or trifluoromethyl;

$R^7$ is $-(CH_2)_n-CO_2R^9$,

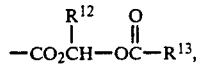

$-NHSO_2CF_3$,

$-SO_3H$, $-C(CF_3)_2OH$,

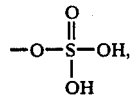

$-PO_3H$,

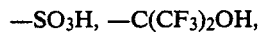

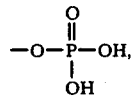

$-CONHOR^{12}$, $-CONHNHSO_2CF_3$, $-(CH_2)_n$-5-tetrazolyl (optionally substituted with $R^9$),

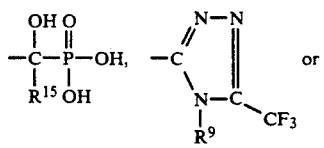

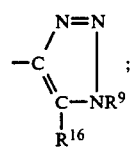

$R^8$ is a single bond, alkyl, alkenyl, aryl, or aralkyl;

$R^9$ is hydrogen, alkyl, cycloalkyl, aryl, aralkyl,

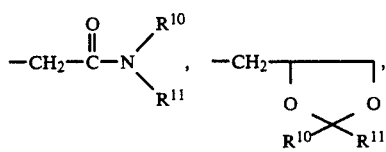

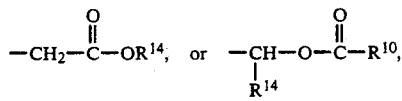

alkali metal or ammonium;

$R^{10}$ and $R^{11}$ are each independently hydrogen, alkyl, alkoxy, cycloalkyl, aryl, or aralkyl, or $R^{10}$ and $R^{11}$ together are $-(CH_2)_2-$, $-(CH_2)_3-$, $-CH=CH-$, or

$R^{12}$ is hydrogen, alkyl, aryl, cycloalkyl, or aralkyl;

$R^{13}$ is alkyl, $-NR^{10}R^{11}$, or

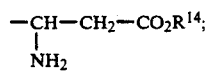

$R^{14}$ is hydrogen, alkyl, perfluoroalkyl, cycloalkyl, phenyl, or benzyl;

$R^{15}$ is hydrogen, alkyl, or phenyl;

$R^{16}$ is $-CN$, $-NO_2$, or $-CO_2R^{14}$; and n is 0, 1, or 2.

For compound I, the following moieties are preferred:

one of $R^1$ and $R^2$ is aralkyl (phenylethyl most preferred) or both $R^1$ and $R^2$ are alkyl (methyl most preferred);

$R^3$ is a single bond;

$R^4$ is alkyl (butyl most preferred);

$R^7$ is $-(CH_2)_n-CO_2R^9$ or 13 $(CH_2)_n$-5-tetrazolyl; and n is 0.

The substituents $R^5$, $R^6$ and $R^2$ are preferred to be attached as in compound I(A) I(A)

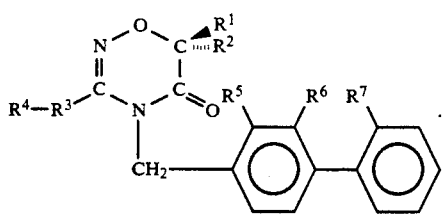 I(A)

DETAILED DESCRIPTION OF THE INVENTION

The present invention relates to the compounds of formula I and to pharmaceutical compositions and methods employing such compounds.

Listed below are definitions of terms used in this specification. These definitions apply to the terms as used throughout this specification, either individually or as part of a larger group, unless otherwise limited in specific instances.

The term "aryl" refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl" refers to straight or branched chain groups having 1 to 10 carbon atoms. Alkyl groups having 1 to 4 carbon atoms are preferred.

The term "cycloalkyl" refers to cyclic hydrocarbon groups having 3 to 7 carbon atoms.

The term "alkoxy" refers to straight or branched chain groups having 1 to 8 carbon atoms. Alkoxy groups having 1 to 3 carbon atoms are preferred.

The term "halogen" refers to fluorine, chlorine, bromine and iodine, with fluorine and chlorine being preferred.

It should be understood that the present invention is meant to include prodrug forms, such as ester, acetal and/or mixed acetal derivatives of compound I. For example, such derivatives have been documented in *Design of Prodrugs,* edited by H. Bundgard, (Elsevier, 1985) and *Methods in Enzymology,* Vol. 42, p. 309–396, edited by K. Widder et al. (Academic Press, 1985). While prodrug forms of compound I are generally represented herein (e.g., when $R^9$ is alkyl), it is understood that any moiety at $R^7$ that will be cleaved in vivo to provide an acidic $R^7$ moiety is within the scope and spirit of this invention.

Compound I may be prepared by the following exemplary process.

A nitrile of the formula $$R^4-R^3-C\equiv N \qquad (II)$$

(e.g., valeronitrile) is converted to the corresponding amideoxime by treatment with hydroxylamine in an aqueous alcohol solvent (e.g., methanol) at about 40° to 60° C. to form a hydroxynitrile amine

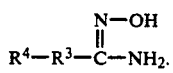 III

Compound III reacts with an alkylating agent

 IV (wherein Y is alkyl, aryl, or aralkyl and X is a leaving group such as bromine, chlorine, methanesulfonate, trifluoromethane sulfonate, and the like) in the presence of a base (e.g., sodium methoxide) in an organic solvent (e.g., methanol) to form an amine-ester

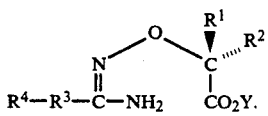 V

Amine-ester V may react upon heating to about 90° to 110° C. or may be treated with a base or catalyst (e.g., trimethylaluminum) in an organic solvent or solvent mixture (e.g., methylene chloride/hexane) to form an oxadiazinone

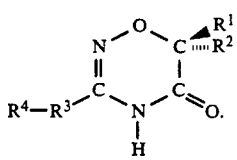 VI

Oxadiazinone VI reacts with a bromo biphenyl

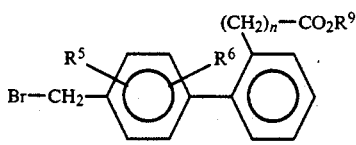 VII (wherein $R^9$ is alkyl, aryl or aralkyl) in the presence of a mild base (e.g., cesium carbonate) in an organic solvent such as dimethylformamide (DMF) to form compound I wherein $R^7$ is $-(CH_2)_n-CO_2R^9$ and $R^9$ is alkyl, aryl, or aralkyl.

Compound I wherein $R^9$ is hydrogen may be obtained by treatment with a de-esterifying agent (e.g., trifluoroacetic acid). Compound I wherein $R^9$ is alkali metal or ammonium can be prepared by treating the corresponding acids with bases such as lithium carbonate or sodium carbonate. Other $R^7$ substituents may be prepared by procedures described in European Patent Application 253,310 (Dupont), published Jan. 20, 1988.

Compounds wherein $R^7$ is $-(CH_2)_n$-5-tetrazolyl may be prepared by reacting compound VI with, in sequence, a bromonitrile

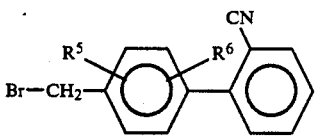 VII' and a trialkyltin azide (e.g., tributyltin azide) in an inert solvent (e.g., xylene) at about 90° to 110° C.

An alternative exemplary process is most useful wherein one of $R^1$ and $R^2$ is aryl. In this alternative process, amideoxime III reacts with phosgene or a phosgene equivalent to form an oxadiazolinone

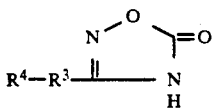

which is regiospecifically alkylated to form an oxadiazolinone-biphenyl ester or nitrile

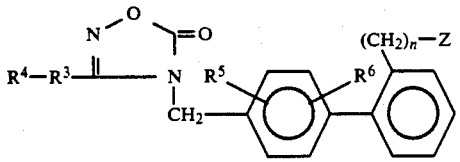

wherein Z is —CN or —$CO_2R^9$ and $R^9$ is alkyl, aryl or aralkyl. Further reaction conditions are described in *Chem. Ber.* 108, 1911 (1975).

Oxadiazolinone-ester IX is saponified and decarboxylated by treatment with a base (e.g., sodium hydroxide) in an aqueous alcohol solvent (e.g., methanol and water) to form an amideoxime

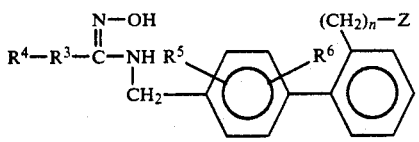

Amideoxime X is treated with alkylating agent IV wherein one of $R^1$ and $R^2$ is aryl (e.g., bromophenylacetate) in the presence of a base (e.g., cesium carbonate) in an organic sovlent (e.g., dimethylformamide) to form diester

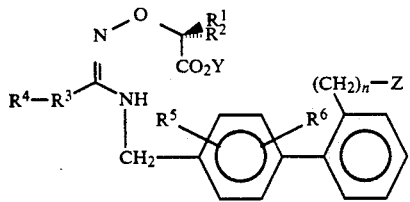

Diester XI is cyclized by treatment with a catalyst (e.g., trimethylaluminum) in an organic solvent or solvent mixture (e.g., hexane/1,2-dichloroethane) with heating at reflux to form compound I wherein $R^7$ is —$(CH_2)_n$—$CO_2R^9$ or the associated nitrile. The nitrile may be converted to tetrazolyl by treatment with a trialkyltin azide (e.g., tributyltin azide) in an inert solvent (e.g., xylene) at about 90° to 110° C.

The compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin-dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy.

The compounds of this invention are also useful in the treatment/prevention of congestive heart failure, cardiac hypertrophy, loss of cognitive function, renal failure and in conjunction with kidney transplant. In addition, in view of the role of these compounds in the renin-angiotensin system described above, the AII antagonist compounds disclosed herein are also expected to be useful for the same or similar indications which have developed for ACE inhibitors.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a peptide of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticryanfen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention may now be further described by the following examples, which are illustrative rather than limiting.

EXAMPLE 1

4'-[(3-Butyl-5,6-dihydro-6-methyl-5-oxo-4H-1,2,4-oxadiazine-4-yl)methyl][1,1'-biphenyl]-2-carboxylic acid A. N-Hydroxypentanimidamide Compound A was prepared by procedures adapted from *Chem. Rev.* 62, 155 (1962) and *Cancer Res.* 38, 1291 (1978).

Sodium carbonate solid (13 g, 123 mmol) was added to a suspension of hydroxylamine hydrochloride (16.7 g, 240 mmol) in methanol (120 mL) and water (60 mL). Gas evolution was observed and a clear solution resulted. Valeronitrile (25 mL, 240 mmol) was then added and the mixture was stirred at 50° C. for 17 hours, after which most of the methanol was removed by distillation in vacuo. The aqueous residue was extracted with dichloromethane (three times); the extract was dried (magnesium sulfate) and concentrated to give compound A as a colorless oil, which solidified on storage at −30° C. (10.4 g, 37%).

B. 2-[[(1-Aminopentylidene)amino]oxy]propanoic acid, methyl ester

Ethyl-2-bromopropionate (0.65 mL, 5.0 mmol) was added to a mixture of compound A (581 mg, 5.0 mmol) and sodium methoxide (300 mg, 5.5 mmol) in methanol (25 mL). The resulting mixture was stirred at 25° C. for 18 hours, after which it was concentrated in vacuo. The residue was dissolved in ethyl acetate/water, extracted with ethyl acetate, dried (magnesium sulfate) and concentrated. The residue was purified by flash chromatogrphy on silica gel (50 g), eluting with ethyl acetate, to give compound B as a yellow oil (270 mg).

C. 3-Butyl-6-methyl-4H-1,2,4-oxadiazin-5(6H)-one

The oil from above (compound B, 260 mg) was dissolved in methylene chloride (10 mL) and a solution of trimethylaluminum in hexane (4.0 mL of 2.0M solution, 8.0 mmol) was added. The resulting mixture was stirred at 25° C. for three hours, after which it was poured into 0.5N hydrochloric acid (100 mL) and extracted with ether. The extract was dried and concentrated to give compound C as a glassy solid (200 mg, 24%).

4'-(Bromomethyl)[1,1'-biphenyl]-2-carboxylic acid, 1,1-dimethylethyl ester

Compound D is prepared as described in European Patent Application 87-109,919.8, Example 85-B.

E.
4'-[(3-Butyl-5,6-dihydro-6-methyl-5-oxo-4H-1,2,4-oxadiazin-4-yl)methyl][1,1'-biphenyl]-2-carboxylic acid, 1,1-dimethylethyl ester A mixture of compound C (180 mg, 1.06 mmol), compound D (400 mg, 1.3 mmol), and cesium carbonate (490 mg, 1.5 mmol) in dimethylformamide (5 mL) was stirred at 25° C. for 30 minutes, after which it was poured into brine and extracted with ethyl acetate. The extract was dried and concentrated; the residue was purified by flash chromatography on silica gel (60 g), eluting with 4:1 hexane:ethyl acetate, to give compound E (360 mg, 78%).

F.
4'-[(3-Butyl-5,6-dihydro-6-methyl-5-oxo-4H-1,2,4-oxadiazin-4-yl)methyl]1,1'-biphenyl]-2-carboxylic acid A solution of compound E (330 mg, 0.75 mmol) in 10 mL trifluoroacetic acid (TFA) was stirred at 25° C. for 45 minutes, after which it was concentrated in vacuo. The residue was purified by preparative HPLC (YMC 30×500 mm S-10 ODS column, eluting with 28 mL/min of 78% aqueous methanol containing 0.1% trifluoroacetic acid). Fractions containing the major product ($\lambda = 300$ nm, retention time of 21 minutes) were combined and concentrated. The residue was triturated with petroleum ether containing a trace of diethyl ether to give Example 1 as a tan solid (54%).

Melting point: 64°–66° C.
Elemental Analysis (%) for 0.29 H$_2$O and 0.035 TFA
Calc'd.: C 68.02; H 6.37; N 7.19; F 0.51.
Found: C 68.02; H 6.31; N 7.11; F 0.50.

EXAMPLE 2

4'-[(3-Butyl-5,6-dihydro-5-oxo-6-phenyl-4H-1,2,4-oxadiazin-4-yl)methyl][1,1'-biphenyl]-2-carboxylic acid A. 2-[[(1-Aminopentylidene)amino]oxy]propanoic acid, ethyl ester Ethyl chloroformate (0.43 mL, 4.5 mmol) was added to a mixture of compound A from Example 1 (500 mg, 4.3 mmol) and pyridine (0.80 mL, 10 mmol) in tetrahydrofuran (10 mL), resulting in an exothermic reaction and formation of a white precipitate. After five minutes, the mixture was heated to reflux and was stirred at reflux for 5 hours. The mixture was then poured into brine, extracted with ethyl acetate (twice), dried (magnesium sulfate), and concentrated in vacuo to give compound A (950 mg).

B. 3-Butyl-4,5-dihydro-5-oxo-1,2,4-oxadiazole

The compound A residue was dissolved in xylene (20 mL), and 2,6-lutidine (0.20 mL) was added. The mixture was heated at reflux for 2 hours, after which the volatiles were distilled off in vacuo. The residue was chromatographed on silica gel (65 g), eluting with 1:1 hexane:ethyl acetate, to give compound B as a tan oil (300 mg, 49%).

C.
4'-[(3-Butyl-4,5-dihydro-5-oxo-1,2,4-oxadiazol-4-yl)methyl][1,1'-biphenyl]-2-carboxylic acid, 1,1-dimethylethyl ester A mixture of compound B (225 mg, 1.5 mmol), compound D from Example 1 (450 mg, 1.5 mmol), and potassium carbonate (275 mg, 1.5 mmol) in dimethylformamide (3 mL) was stirred at 25° C. for 7 hours, after which it was poured into brine and extracted with ethyl acetate (twice). The extract was dried (magnesium sulfate) and concentrated. The residue was purified by chromatography on silica gel (65 g), eluting with 3:1 hexane:ethyl acetate, to give compound C as a colorless oil (375 mg, 62%).

D.
4'-[[[1-(Hydroxyimino)pentyl]amino]methyl]-[1,1'-biphenyl]-2-carboxylic acid, 1,1-dimethylethyl ester A mixture of compound C (880 mg, 2.15 mmol), methanol (10 mL), and 1N sodium hydroxide solution (5 mL) was stirred at 25° C. for 24 hours, after which it was poured into water and the pH was adjusted to 7.0. The mixture was then extracted with ethyl acetate, and the extract was dried and concentrated. The residue was purified by flash chromatography on silica gel (300 g, eluting with ethyl acetate) to give compound D as a clear oil (500 mg, 61%).

E.
4'-[[[1-[(2-Methoxy-2-oxo-1-phenylethoxy)-imino]pentyl]amino]methyl]-[1,1'-biphenyl]-2-carboxylic acid, 1,1-dimethylethyl ester A mixture of compound D (375 mg, 0.98 mmol), methyl-α-bromophenylacetate (343 mg, 1.5 mmol), and cesium carbonate (650 mg, 2.0 mmol) in dimethylformamide (2 mL) was stirred at 25° C. for 18 hours, after which it was poured into brine and extracted with ethyl acetate. The extract was dried and concentrated, and the residue was purified by flash chromatography on silica gel (60 g, eluting with 4:1 hexane:ethyl acetate) to give compound E as a clear colorless oil (280 mg, 54%).

F.
4'-[(3-Butyl-5,6-dihydro-5-oxo-6-phenyl-4H-1,2,4-oxadiazin-4-yl)methyl][1,1'-biphenyl]-2-carboxylic acid Trimethylaluminum solution (1.0 mL of 2.0 molar solution in hexanes, 2.0 mmol) was added to a solution of compound E (190 mg, 0.36 mmol) in 1,2-dichloroethane (10 mL). The resulting mixture was heated at reflux for 3 hours, after which it was poured into 0.3N hydrochloric acid, extracted with methylene chloride, dried, and concentrated. The residue was passed through a short column of silica gel, eluting with 3:1 hexane:ethyl acetate, and the eluant was partitioned into three fractions based on TLC $R_f$ in the same solvent system. The two highest $R_f$ fractions ($R_f > 0.4$) were combined and concentrated to give an oily residue (38 mg). The residue was dissolved in trifluoroacetic acid (1 mL), stirred for one hour, and concentrated in vacuo. The residue was purified by preparative HPLC (YMC S-10 ODS column, 30×500 mm, eluting with 30 mL/min of a linear gradient from 50% to 90% aqueous methanol containing 0.1% trifluoroacetic acid). All fractions showing UV absorbance at 254 nm were reanalyzed by analytical HPLC; two major products were found. Fractions 46 and 47 were concentrated in vacuo to give Example 2 (4 mg), which was lyophilized from ethanol/water to give a tan solid (3 mg).

Elemental Analysis (%) for 1.5 H$_2$O
Calc'd: C 69.07; H 6.23;N 5.97.
Found: C 69.47; H 6.59;N 5.47.

EXAMPLE 3
4'-[(3-Butyl-5,6-dihydro-5-oxo-4H-1,2,4-oxadiazin-4-yl)methyl]1,1'-biphenyl]-2-carboxylic acid

A. 2-[[(1-Aminopentylidene)amino]oxy]ethanoic acid, methyl ester

Methyl bromoacetate (1.42 mL, 15.0 mmol) was added to a mixture of compound A from Example 1 (1.16 g, 10 mmol) cesium carbonate (6.5 g, 20 mmol) in dimethylformamide (50 mL), and stirred at room temperature for 18 hours. The mixture was poured into water (300 mL), extracted with ethyl acetate (3×200 mL), dried (magnesium sulfate), and concentrated in vacuo to provide compound A as an amber oil.

B. 3-Butyl-4H-1,2,4-oxadiazin-5(6H)-one

The crude compound A was dissolved in methylene chloride (150 mL) under argon, and a solution of trimethylaluminum in hexane (25 mL of a 2.0M solution, 50 mmol) was added. The resulting mixture was stirred for 6 hours, after which it was poured into cold 0.5N hydrochloric acid (300 mL), and extracted with methylene chloride (3×300 mL). The crude extract was purified using flash chromatography (200 g silica gel eluted with 3:1 hexane:ethyl acetate), and fractions containing the major product were combined and concentrated in vacuo to give compound B as a yellow waxy solid (1.112 g, 7.1 mmol, 71%).
Melting point: 55°–57° C.

C.
4'-[(3-Butyl-5,6-dihydro-5-oxo-4H-1,2,4-oxadiazin-4-yl)methyl][1,1'-biphenyl-2-carboxylic acid, 1,1-dimethylethyl ester A mixture of compound B (156 mg, 1 mmol), compound D from Example 1 (400 mg, 1 mmol), and potassium carbonate (276 mg, 2 mmol) was stirred in dimethylformamide (5 mL) at room temperature for 18 hours, after which it was poured into water (100 mL), extracted with ethyl acetate, dried (magnesium sulfate), and concentrated to an oil in vacuo. The crude material was purified by flash chromatography on silica gel (65 g, eluted with 5:1 hexane:ethyl acetate) to provide compound C as a colorless oil (231 mg, 55%).

4'-[(3-Butyl-5,6-dihydro-5-oxo-4H-1,2,4-oxadiazon-4-yl)methyl][1,1'-biphenyl]-2-carboxylic acid Compound C (221 mg, 0.52 mmol) was dissolved in dichloromethane (20 mL) and trifluoroacetic acid (20 mL) and stirred at room temperature for 1.5 hours. The solution was concentrated in vacuo and purified using preparative HPLC (YMC 30×500 mm S-10 ODS column, eluting with 50 mL/min of 80% aqueous methanol containing 0.1% trifluoroacetic acid) and then lyophilized from ethanol/water to provide Example 3 as an off-white solid (110 mg, 0.31 mmol, 60%).
Melting point: 125°–130° C.
Elemental Analysis (%) for 1.0 H$_2$O
Calc'd: C 65.61; H 6.29;N 7.29.
Found: C 65.52; H 6.00;N 7.36.

EXAMPLE 4
4'-[[3-Butyl-5,6-dihydro-5-oxo-6-(phenylmethyl)-4H-1,2,4-oxadiazin-4-yl]methyl][1,1'-biphenyl-2carboxylic acid

A. 2-Bromo-3-benzenepropanoic acid

The following procedure was adapted from *JCS Perkin I,* 2140 (1979).

To a solution of d,l-phenylalanine (16.52 g, 100 mmol) and sodium bromide (34 g, 330 mmol), in an aqueous solution of sulfuric acid (3N, 165 mL) cooled to 0°–4° C., was added an aqueous solution of sodium nitrite (9.66 g, 140 mmol in 50 mL of water). The mixture was stirred at 5° C. for an additional hour, warmed to room temperature and stirred for one hour. The mixture was extracted with diethyl ether (3×250 mL), washed with water (2×200 mL) dried (magnesium sulfate) and concentrated in vacuo to yield a yellow oil, which was used without further purification (18 g, 79 mmol, 79%).

B. Ethyl-2-Bromo-3-benzenepropanoate

To a solution of compound A (18 g, 79 mmol) and dimethylformamide (55 mg, 0.75 mmol) in dichloromethane (160 mL) cooled to 5° C. was added a solution of oxalyl chloride (80 mL, 2M in dichloromethane). After stirring for thirty minutes at 5° C., the solution was warmed to room temperature and stirred for an additional two hours. Ethanol (100 mL, absolute) was added slowly to the solution and after 15 minutes, the mixture was heated to reflux and held there for two hours. The ethanol was removed by distillation and the desired product was isolated by vacuum distillation (107°–115° C. at 0.5 mm Hg) as a colorless oil (12.63 g, 49 mmol, 62%).

C. 3-Butyl-6-benzyl-4H-1,2,4-oxadiazin-5(6H)one

Compound A from Example 1 (1.16 g, 10 mmol), compound B (3.85 g, 15 mmol), and cesium carbonate (6.5 g, 20 mmol) was stirred in dimethylformamide (50 mL) for 18 hours at room temperature. The mixture was poured into water (200 mL), extracted with ethyl acetate (3×200 mL), dried (magnesium sulfate), and concentrated in vacuo to an amber oil. The oil was dissolved in dichloromethane (200 mL) under argon, and a solution of trimethylaluminum (25 mL, 2M in hexanes) was added over period of fifteen minutes. The mixture was allowed to stir for an additional 18 hours and then poured into a cold aqueous hydrochloric acid solution (500 mL, 0.5N). Extraction of the aqueous solution using dichloromethane (3×300 mL) and subsequent purification using flash chromatography (250 g silica, 5:1, followed by 2:1 hexane:ethyl acetate) provided the desired product as a white solid. Melting point: 82°–85° C. (490 mg, 2 mmol).

D. 4'-[(3-Butyl-5,6-dihydro-6-benzyl-5-oxo-4H-1,2,4-oxadiazin-4-yl)methyl][1,1'-biphenyl]-2-carboxylic acid, 1,1-dimethylethyl ester Compound C (245 mg, 1 mmol), compound D from Example 1 (400 mg, 1 mmol), potassium carbonate (276 mg, 2 mmol) and dimethylformamide (5 mL) were combined and stirred at room temperature for 18 hours, and then at 45° C. for an additional 3 hours. The mixture was poured into water (150 mL), extracted with ethyl acetate (2×150 mL), dried (magnesium sulfate) and concentrated in vacuo. This crude material was purified using flash chromatography (60 g silica, eluted with 5:1 hexane:ethyl acetate) to provide compound D as a glassy solid (300 mg, 0.58 mmol, 58%).

E. 4'-[[3-Butyl-5,6-dihydro-5-oxo-6-(phenylmethyl)-4H-1,2,4-oxadiazin-4-yl]methyl][1,1'-biphenyl-2-carboxylic acid Compound D (300 mg, 0.58 mmol) was stirred in dichloromethane (20 mL) and trifluoroacetic acid, (20 mL) for two hours, and then concentrated in vacuo to provide the crude product. This material was purified by preparative HPLC (YMC 30×500 mm S-10 ODS column, eluting with 50 mL/min of 85% aqueous methanol containing 0.1% trifluoroacetic acid) and then lyophilized from ethanol/water to provide Example 4 as a white solid (228 mg, 0.5 mmol, 86%).
Melting point: 148°–150° C.
Elemental Analysis (%) for 0.4 H$_2$O +0.05 TFA
Calc'd: C 71.89; H 6.19; N 5.97; F 0.61.
Found: C 71.85; H 6.06; N 6.02; F 0.57.

EXAMPLE 5

4'-[(3-Butyl-5,6-dihydro-6,6-dimethyl-5-oxo-4H-1,2,4-oxadiazin-4-yl)methyl][1,1'-biphenyl]-2carboxylic acid

A. 3-Butyl-6,6-di-methyl-4H-1,2,4-oxadiazin-5(6H)-one

The following procedure was adapted from *Heterocycles* 26, 163 (1987).

To a solution of compound A from Example 1 (580 mg, 5.0 mmol) in tetrahydrofuran (5 mL) was added 2-bromo-2-methylpropionyl bromide (0.62 mL, 5 mmol). The resulting mixture was stirred at 25° C. for 30 minutes, after which sodium hydride solid was slowly added (600 mg of 60% suspension in oil, 15 mmol), and the mixture was stirred for an additional 2 hours. The mixture was then poured into excess 0.5N hydrochloric acid, extracted with ethyl acetate, dried (magnesium sulfate), and concentrated. The residue was purified by flash chromatography on silica gel (65 g, eluting with 3:1 hexane:ethyl acetate); fractions containing material positive to Rydon stain were combined, concentrated, dissolved in 1:1 ether:petroleum ether, filtered, and reconcentrated to give compound A as a clear, colorless oil (96 mg, 10% yield).

B. 4'-[(3-Butyl-5,6-dihydro-6,6-dimethyl-5-oxo-4H-1,2,4-oxadiazin-4-yl)methyl][1,1-biphenyl]-2-carboxylic acid, 1,1-dimethylethyl ester Compound A (96 mg, 0.52 mmol), compound D from Example 1 (252 mg, 0.62 mmol), and cesium carbonate (338 mg, 1.04 mmol) were stirred in dimethylformamide (5 mL) at room temperature under argon for 18 hours. The mixture was poured into water (100 mL), extracted with ethyl acetate, dried (magnesium sulfate), and concentrated in vacuo to yield a yellow oil that was purified by flash chromatography (65 g silica gel eluted with hexane:ethyl acetate 6:1). Compound B was isolated as a colorless oil (115 mg, 49%).

C. 4'-[(3-Butyl-5,6-dihydro-6,6-dimethyl-5-oxo-4H-1,2,4-oxadiazin-4-yl)methyl][1,1-biphenyl]-2-carboxylic acid Compound B (115 mg, 0.25 mmol) was stirred in a solution of dichloromethane (10 mL) and trifluoroacetic acid (10 mL) for 2.5 hours and then concentrated to a brown oil in vacuo. The residue was purified by preparative HPLC (YMC 30×500 mm S-10 ODS column, eluting with 50 mL/min of 85% aqueous methanol containing 0.1% trifluoroacetic acid). Fractions containing the major product were combined and concentrated in vacuo to yield Example 5 as a white solid (72 mg, 0.18 mmol, 72%).
Melting point: 152°–154° C.
Elemental Analysis (%) for 0.25 H$_2$O
Calc'd: C 69.24; H 6.70; N 7.02.
Found: C 69.24; H 6.71; N 6.90.

EXAMPLE 6

4'-[[3-Butyl-5,6-dihydro-5-oxo-6-(2-phenylethyl)-4H-1,2,4-oxadiazin-4-yl]methyl][1,1'-biphenyl]-2carboxylic acid

A. 2-[[(1-Aminopentylidene)amino]oxy]-4-phenylbutanoic acid, methyl ester

Ethyl-2-bromo-4-phenylbutanoate (1.694 g, 6.25 mmol) was added to a mixture of compound A from Example 1 (581 mg, 5 mmol) and cesium carbonate (3.258 g, 10 mmol) in dimethylformamide (5 mL), and stirred at room temperature for 18 hours. The mixture was poured into water (300 mL), extracted with ethyl acetate (3×200 mL), dried (magnesium sulfate), and concentrated in vacuo to provide compound A as an amber oil.

B. 3-Butyl-6-(2-phenylethyl)-4H-1,2,4-oxadiazin-5(6H)-one

The crude compound A was dissolved in methylene chloride (25 mL) under argon, and a solution of trimethylaluminum in hexane (20 mL of a 2.0M solution, 40 mmol) was added. The resulting mixture was stirred 2.5 hours, after which it was poured into 0.5N hydrochloric acid (300 mL), and extracted with methylene chloride (3×300 mL). The crude extract was purified using flash chromatography (200 g silica gel eluted with 4:1 hexane:ethyl acetate) dried, and concentrated to give compound B as a yellow, waxy solid (594 mg, 2.28 mmol, 46%).

Melting point: 75°–77° C.

C.

4'-[(3-Butyl-5,6-dihydro-6-(2-phenylethyl)-5-oxo-4H-1,2,4-oxadiazin-4-yl)methyl][1,1'-biphenyl]-2-carboxylic acid, 1,1-dimethylethyl ester A mixture of compound B (260 mg, 1 mmol), compound D from Example 1 (480 mg, 1.2 mmol), and cesium carbonate (650 mg, 2 mmol) was stirred in dimethylformamide (5 mL) at room temperature for 18 hours. The mixture was then poured into water (100 mL), extracted with ethyl acetate, dried (magnesium sulfate), and concentrated to an oil in vacuo. The crude material was purified by flash chromatography on silica gel (60 g, eluted with 10:1 hexane:ethyl acetate) to provide compound C as a colorless oil (500 mg, 94%).

D.

4'-[[3-Butyl-5,6-dihydro-5-oxo-6-(2-phenylethyl)-4H-1,2,4-oxadiazin-4-yl]methyl][1,1'-biphenyl]-2-carboxylic acid Compound C (460 mg, 0.87 mmol) was dissolved in dichloromethane (20 mL) and trifluoroacetic acid (20 mL) and stirred at room temperature for 1.5 hours. The solution was concentrated in vacuo and purified using preparative HPLC (YMC 30×500 mm S-10 ODS column, eluting with 50 mL/min of 78% aqueous methanol containing 0.1% trifluoroacetic acid) and then lyophilized from ethanol/water to provide Example 6 as a yellow solid (335 mg, 0.71 mmol, 81%).

Melting point: 74°–b 80° C.
Elemental Analysis (%) for 0.25 $H_2O$
Calc'd: C 73.32; H 6.47; N 5.90.
Found: C 73.32; H 6.44; N 5.75.

EXAMPLE 7

3-Butyl-6-(2-phenylethyl)-4-[[2'-(1H-tetrazol-5-yl)-[1,1'-biphenyl]-4-yl]methyl]-4H-1,2,4-oxadiazin-5(6H)-one

A.

3-Butyl-6-(2-phenylethyl)-4-[4-(2-cyanophenyl)benzyl]-4H-1,2,4-oxadiazin-5(6H)-one A mixture of compound B from Example 6 (390 mg, 1.5 mmol), 4'-bromomethyl-2-cyanobiphenyl (408 mg, 1.5 mmol, prepared as described in U.S. Pat. No. 4,880,804), cesium carbonate (975 mg, 3.0 mmol) and dimethylformamide (5 mL) was stirred under argon at room temperature for 18 hours. The mixture was poured into water (150 mL), extracted with ethyl acetate (2×150 mL), dried (magnesium sulfate) and concentrated in vacuo to an amber oil. The crude residue was purified by flash chromatography (65 g Sorbisil silica eluted with 3:1 hexane:ethyl acetate) to provide compound A as a colorless oil (yield 400 mg, 0.89 mmol, 60%).

B.

3-Butyl-6-(2-phenylethyl)-4-[[2'-(1H-tetrazol-5-yl)-[1,1'-biphenyl]-4-yl]methyl]-4H-1,2,4-oxadiazin-5(6H)-one A solution of compound A (400 mg, 0.89 mmol), tributyltinazide (886 mg, 2.67 mmol) and O-xylene (0.5 mL) was stirred at 100° C. for 18 hours. After cooling to room temperature, the solution was purified by flash chromatography (65 g Sorbisil silica eluted with 60:40:1 hexane:ethyl acetate:acetic acid) to produce an amber oil. Thin layer chromatography analysis (20:1 ethyl acetate:(pyridine:20 acetic acid:6, water:11), phosphomolybdic acid stain) revealed a remaining impurity that was eliminated by passing the mixture through a second flash chromatography column (65 g Sorbisil silica, eluant as described for thin layer chromatography above). The residue thus obtained was dissolved in methanol (10 mL), adjusted to pH 10.5 (0.1% potassium carbonate) and eluted through a polystyrene preparative HPLC column (Jordi-gel column, water to methanol gradient). Fractions containing the major product were combined, concentrated at low heat in vacuo, dissolved in water (10 mL) and lyophilized. Example 7 was obtained as a white solid (134 mg).

Melting point: 56°–65° C.
Elemental Analysis (%) for 1.7 $H_2O$
Calc'd: C 61.83; H 5.80; N 14.92.
Found C 61.83; H 5.45; N 14.64.

EXAMPLE 8

(S)-4'-[[3-Butyl-5,6-dihydro-5-oxo-6-(2-phenyl-ethyl)-4H-1,2,4-oxadiazin-4-yl]methyl][1,1'-biphenyl]2-carboxylic acid The following procedure was adapted from *Chem. Pharm. Bull.* 37, 280 (1989).

To a solution of (−)-α-amino-4-phenylbutyric acid (1.79 g, 10 mmol) in sulfuric acid (20 mL, 3N) at 4° C. was added a solution of sodium nitrite (966 mg, 14 mmol in 15 mL water) over a period of fifteen minutes. The solution was allowed to warm to room temperature with continued stirring for 24 hours. Additional sulfuric acid (10 mL, 3N) was added and the solution was heated to reflux with subsequent addition of sodium nitrite (1.93 g in 15 mL water). The solution was then allowed to cool to room temperature and was extracted with ether (2×250 mL), dried (magnesium sulfate), and concentrated in vacuo to a colorless solid (1.11 g, 6.16 mmol, 62%).

Melting point: 103°–108° C.
$[\alpha]_D$ −16.3 (c=0.9, trichloromethane).

B. (−)-α-Hydroxy-4-phenylbutyric acid, ethyl ester

The following procedure was adapted from *Chem. Pharm. Bull.* 37, 280 (1989).

Thionyl chloride (1.08 mL, 14.78 mmol) was added to a solution of compound A (1.11 g, 6.16 mmol) in ethanol (15 mL absolute) stirred at 4° C. The solution was allowed to warm to room temperature and stirred for an additional 18 hours, at which point the thionyl chloride and ethanol were removed in vacuo and the remaining residue was dissolved in ethyl acetate (200 mL), washed with sodium bicarbonate (200 mL saturated aqueous solution), water (200 mL), and brine (200 mL). The extract was concentrated in vacuo and compound B was isolated as an amber oil, (905 mg, 4.35 mmol, 71%) and used without further purification. $[\alpha]_D$ −18.9

(c=2.9, trichloromethane) (lit. [α]$_D$−22.1 (c=1, trichloromethane)).

C.
(−)-α-[(Trifluoromethyl)sulfonyl]oxy-4-phenylbutyric acid, ethyl ester The following procedure was adapted from *Tet. Lett.*, 25, 1143 (1984).

To a solution of compound B (208 mg, 0.5 mmol) and pyridine (40 μL, 0.5 mmol) in dichloromethane (2.5 mL) cooled to 0° C. was added trifluoromethanesulfonic anhydride (96 μL, 0.57 mmol). After stirring for 45 minutes, a precipitate formed and was removed by filtration (0.45 μm nylon millipore type). The remaining solution was concentrated in vacuo to a volume of 0.5 mL of compound C without further purification.

D.
2-[[(1-Aminopentylidene)amino]oxy]-4-phenylbutanoic acid, methyl ester The crude compound C was added to a solution of compound A from Example 1 (58 mg, 0.5 mmol) and triethylamine (70 μL, 0.5 mmol) in dichloromethane (2.5 mL) and stirred at room temperature for two hours. The solution was poured into water (50 mL), extracted with dichloromethane (2×50 mL), dried (magnesium sulfate) and concentrated in vacuo to provide compound D.

E.
3-Butyl-6-(2-phenylethyl)-4H-1,2,4-oxadiazin-5(6H)-one

Compound D, without purification, was dissolved in dichloromethane (5 mL) and a solution of trimethylaluminum (0.5 mL, 1 mmol, 2M in hexanes) was added. After stirring for four hours at room temperature, the solution was poured into hydrochloric acid (200 mL, 0.5N at 0° C.), extracted with dichloromethane (2×200 mL), concentrated in vacuo, and purified by flash chromatography (30 g Merck silica gel eluted with hexane:ethyl acetate 4:1) to yield compound E (50 mg, 38%) as a colorless oil. [α]$_D$+9.38, (c=0.3, trichloromethane).

F.
(S)-4′-[[3-Butyl-5,6-dihydro-5-oxo-6-(2-phenylethyl)-4H-1,2,4-oxadiazin-4-yl]methyl][1,1′-biphenyl]-2-carboxylic acid, 1,1-dimethylethyl ester Compound E (44 mg, 0.17 mmol), compound D from Example 1 (82 mg, 0.20 mmol) and cesium carbonate (110 mg, 0.34 mmol) were stirred for 18 hours at room temperature in dimethylformamide (1 mL). The mixture was poured into water (100 mL), extracted with ethyl acetate (2×100 mL), dried (magnesium sulfate), and concentrated in vacuo. The crude residue was purified using flash chromatography (12 g Merck silica eluted with hexane:ethyl acetate 9:1) and isolated as a colorless oil (61 mg, 0.12 mmol, 68%).

G.
(S)-4′-[[3-Butyl-5,6-dihydro-5-oxo-6-(2-phenylethyl)-4H-1,2,4-oxadiazin-4-yl]-methyl][1,1′-biphenyl]-2-carboxylic acid Compound F (61 mg, 0.12 mmol) was stirred at room temperature in a solution of dichloromethane (10 mL) and trifluoroacetic acid (10 mL) for 2 hours. The solution was concentrated in vacuo and the residue was purified using preparative HPLC (conditions: YMC S-10 ODS column 30 mm×500mm eluted at 50 mL/min with 84% aqueous methanol containing 0.1% trifluoroacetic acid, monitored at 254 nanometers). The residue obtained after concentration of preparative HPLC fractions in vacuo was dissolved in water (50 mL) and ethanol (5 mL), and lyophilized to give Example 8 as a white solid (45 mg, 0.1 mmol, 82%).

Melting point: 65°-70° C.

[α]$_D$= +47.6° (c=0.1, chloroform)

Elemental Analysis (%) for 0.6 H$_2$O +0.2 TFA

Calc'd: C 70.04; H 6.28;N 5.56; F 2.26.

Found: C 69.94; H 6.10;N 5.29; F 1.90.

What is claimed is:

1. A compound of the formula

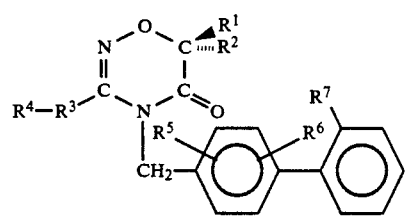

and pharmaceutically acceptable salts and prodrugs thereof, wherein:

$R^1$ and $R^2$ are each independently hydrogen, alkyl, aryl, aralkyl, cycloalkyl, cycloalkylalkyl, thiophenalkyl, pyridylalkyl, or —$R^8CO_2R^9$;

$R^3$ is a single bond, —S—, or —O—;

$R^4$ is hydrogen, alkyl, alkenyl, alkynyl, aryl, cycloalkyl, aralkyl, cycloalkylalkyl, or thiophenalkyl;

$R^5$ and $R^6$ are each independently hydrogen, alkyl, alkoxy, halogen, or trifluoromethyl;

$R^7$ is —(CH$_2$)$_n$—CO$_2R^9$,

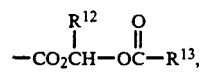

—NHSO$_2$CF$_3$,

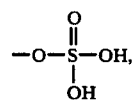

—SO$_3$H, —C(CF$_3$)$_2$OH,

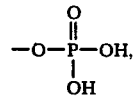

—PO$_3$H

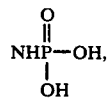

—CONHOR$^{12}$, —CONHNHSO$_2$CF$_3$, —(CH$_2$)$_n$-5H tetrazolyl (optionally substituted with R$^9$),

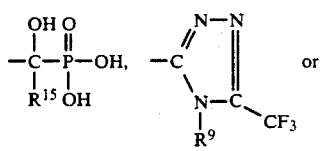

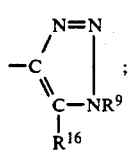

$R^8$ is a single bond, alkyl, alkenyl, aryl, or aralkyl;
$R^9$ is hydrogen, alkyl, cycloalkyl, aryl, aralkyl,

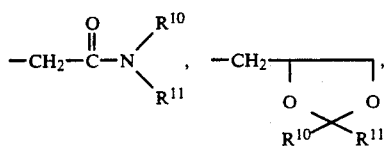

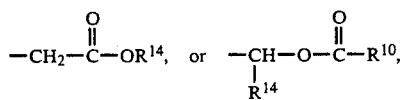

alkali metal or ammonium;
$R^{10}$ and $R^{11}$ are each independently hydrogen, alkyl, alkoxy, cycloalkyl, aryl, or aralkyl, or $R^{10}$ and $R^{11}$ together are —$(CH_2)_2$—, —$(CH_2)_2$—, —CH=CH—, or

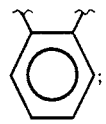

$R^{12}$ is hydrogen, alkyl, aryl, cycloalkyl, or aralkyl;
$R^{13}$ is alkyl, —$NR^{10}R^{11}$, or

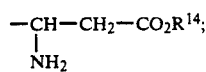

$R^{14}$ is hydrogen, alkyl, perfluoroalkyl, cycloalkyl, phenyl, or benzyl;
$R^{15}$ is hydrogen, alkyl, or phenyl;
$R^{16}$ is —CN, —$NO_2$, or —$CO_2R^{14}$; and n is 0, 1, or 2.

2. The compound of claim 1, wherein one of $R^1$ and $R^2$ is aralkyl.

3. The compound of claim 1, wherein one of $R^1$ and $R^2$ is phenylethyl.

4. The compound of claim 1, wherein $R^1$ and $R^2$ are each alkyl.

5. The compound of claim 1, wherein $R^1$ and $R^2$ are each methyl.

6. The compound of claim 1, wherein $R^3$ is a single bond and $R^4$ is alkyl.

7. The compound of claim 1, wherein $R^2$ is a single bond and $R^4$ is butyl.

8. The compound of claim 1, wherein $R^7$ is $(CH_2)_n$-tetrazolyl and n is 0.

9. The compound of claim 1 having the structure

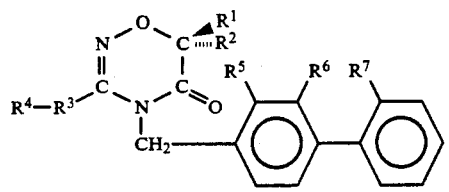

10. The compound of claim 1, selected from the group consisting of:
4'-[(3-Butyl-5,6-dihydro-6-methyl-5-oxo-4H-1,2,4-oxadiazin-4-yl)methyl][1,1'-biphenyl]-2carboxylic acid;
4'-[(3-Butyl-5,6-dihydro-5-oxo-6-phenyl-4H-1,2,4-oxadiazin-4-yl)methyl][1,1'-biphenyl]-2carboxylic acid;
4'-[(3-Butyl-5,6-dihydro-5-oxo-4H-1,2,4-oxadiazin-4-yl)methyl]1,1'-biphenyl]-2carboxylic acid;
4'-[3-Butyl-5,6-dihydro-5-oxo-6-(phenyl-methyl)-4H-1,2,4-oxadiazin-4-yl]methyl][1,1'-biphenyl-2-carboxylic acid;
4'-[(3-Butyl-5,6-dihydro-6,6-dimethyl-5-oxo-4H-1, 2,4-oxadiazin-4-yl)methyl][1,1'-biphenyl-2-carboxylic acid;
4'-[[3-Butyl-5,6-dihydro-5-oxo-6-(2-phenylethyl)-4H-1,2,4-oxadiazin-4-yl]methyl][1,1'-biphenyl]-2-carboxylic acid;
3-Butyl-6-(2-phenylethyl)-4-[[2'-(1H-tetrazol-5-yl)-[1,1'-biphenyl]-4-yl]methyl]-4H-1,2,4-oxadiazin-5(6H)-one; and
(S)-4'-[[3-Butyl-5,6-dihydro-5-oxo-6-(2-phenylethyl)-4-yl]methyl][1,1'-biphenyl]-4H-1,2,4-oxadiazin-4-yl]methyl][1,1'-biphenyl]-2-carboxylic acid.

11. A method of treating hypertension comprising administering to a mammal in need thereof a therapeutically effective amount of a compound of claim 1.

12. A method of treating congestive heart failure comprising administering to a mammal in need thereof a therapeutically effective amount of a compound of claim 1.

13. A method for preventing cardiac hypertrophy comprising administering to a mammal in need thereof a therapeutically effective amount of a compound of claim 1.

* * * * *